United States Patent
Leber

(10) Patent No.: US 6,560,894 B2
(45) Date of Patent: May 13, 2003

(54) TURKEY TAIL DRYING DEVICE

(76) Inventor: Mark David Leber, 698 Hazelton Dr., Madison, MS (US) 39110

( * ) Notice: Subject to any disclaimer, the term of this patent is extended or adjusted under 35 U.S.C. 154(b) by 0 days.

(21) Appl. No.: 09/944,773

(22) Filed: Sep. 4, 2001

(65) Prior Publication Data

US 2003/0046827 A1 Mar. 13, 2003

(51) Int. Cl.$^7$ .............................................. D06M 11/00
(52) U.S. Cl. .............................. 34/280; 34/237; 34/239; 34/442; 34/103; 248/346.03
(58) Field of Search ..................... 34/280, 237, 239, 34/442, 103, 107; 428/542.2, 542.4, 542.6, 16, 913.3; 434/296; 426/480; 248/176.1, 346.01, 346.03

(56) References Cited

U.S. PATENT DOCUMENTS

| | | | | | |
|---|---|---|---|---|---|
| 2,729,452 | A | * | 1/1956 | Baumann | 248/441.1 |
| 4,350,318 | A | * | 9/1982 | Gallis | 249/219.2 |
| 4,407,523 | A | * | 10/1983 | Campione | 248/453 |
| 4,583,454 | A | * | 4/1986 | Huang et al. | 126/21 A |
| 4,717,626 | A | * | 1/1988 | Badger | 428/16 |
| 5,064,725 | A | * | 11/1991 | Acker | 428/16 |
| 5,343,634 | A | * | 9/1994 | Dailey | 34/104 |
| 5,419,304 | A | * | 5/1995 | Pardue | 124/86 |
| 5,437,935 | A | * | 8/1995 | Fredeen | 428/16 |
| 5,653,217 | A | * | 8/1997 | Keller | 124/87 |

* cited by examiner

*Primary Examiner*—Ira S. Lazarus
*Assistant Examiner*—Andrea M. Ragonese

(57) ABSTRACT

This device aids in the drying or curing process of a turkey tail. The device consists of a flat surface (back plate) with holes and dowels to tack the individual primary turkey tail feathers in a desired drying position. Also, the lower section of the back plate consists of a tray used to contain a chemical that will hasten the drying time. A stabilizing block is placed in the chemical tray over the meaty part of the turkey tail and fastened to the back plate with a bolt and wing nut. The device and the turkey tail can then be placed upright in a small space, or hung on a nail or screw using the slot on the rear of the back plate, for the drying duration.

15 Claims, 3 Drawing Sheets

TURKEY TAIL DRYING DEVICE

REFERENCE TO A MICROFICHE APPENDIX

Not Applicable

BACKGROUND OF THE INVENTION

When a turkey hunter harvests a wild turkey, the turkey tail is extracted from the carcass by cutting at the base of the tail. The turkey tail is then tacked to a flat surface, in a desired position to dry or cure before mounting. Having a surface to dry a turkey tail is most times cumbersome, often non-reusable, or difficult to store. These surfaces usually consist of, but are not limited to, a sheet of plywood, a door, or a wall. A chemical, typically salt or Clorox powder, is used on the meaty part of the turkey tail to hasten the drying time. The drying period is usually a week or more. After sufficient drying, the turkey tail is taken off the drying surface. The turkey tail will retain the drying position for the life of the tail. The turkey tail can then be mounted on one of many mounting devices/kits on the market and displayed on a wall as a trophy, as presented in Fredeen, U.S. Pat. No. 5,437,935, and in Acker, U.S. Pat. No. 5,064,725. Deer horns are mounted on a plaque in a similar fashion as presented in Badger, U.S. Pat. No. 4,717,626.

BRIEF SUMMARY OF THE INVENTION

The present invention is a device used in the drying or curing process of a turkey tail. The invention includes a flat surface (back plate) with a chemical tray, a stabilizing block, a plurality of dowels, a bolt, and a wing nut. The dowels are used to tack the primary tail feathers of the turkey to the back plate. The chemical tray is used to contain excess drying powder or liquid. The bolt and wing nut secure the turkey tail and stabilizing block to the back plate. The present invention is a device that is small in nature, easy to store, reusable, and simple to use. Reference to the present invention is depicted in Leber, Disclosure Document No. 496835.

DETAILED DESCRIPTION OF THE INVENTION

Figure 1:
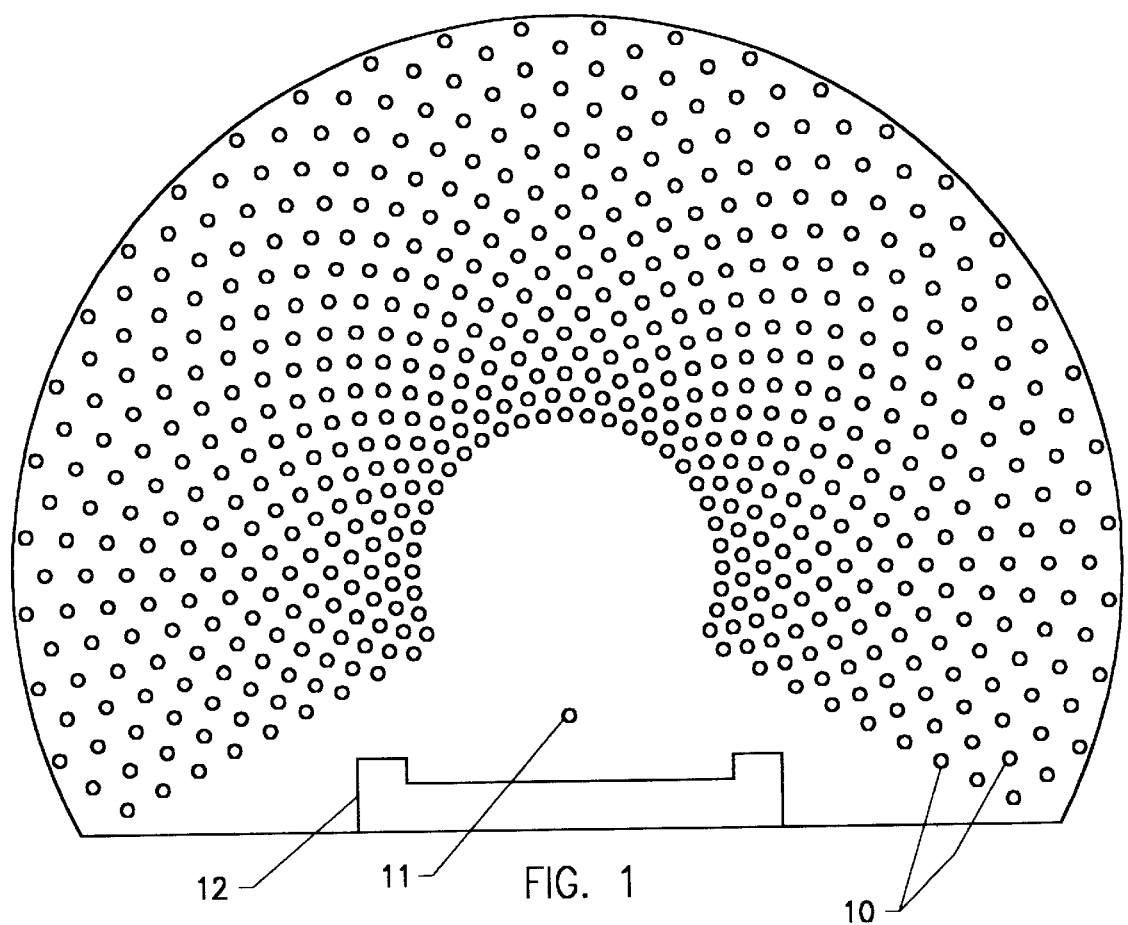
FIG. 1 is a plan view of a flat surface (back plate) with chemical tray in accordance with the preferred embodiment of the invention.
Figure 2:
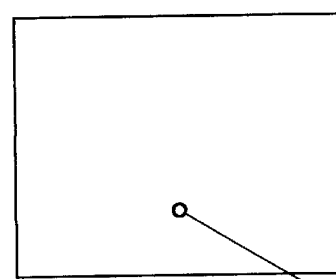
FIG. 2 is a plan view of a block in accordance with the preferred embodiment of the invention.
Figures 4, 5:
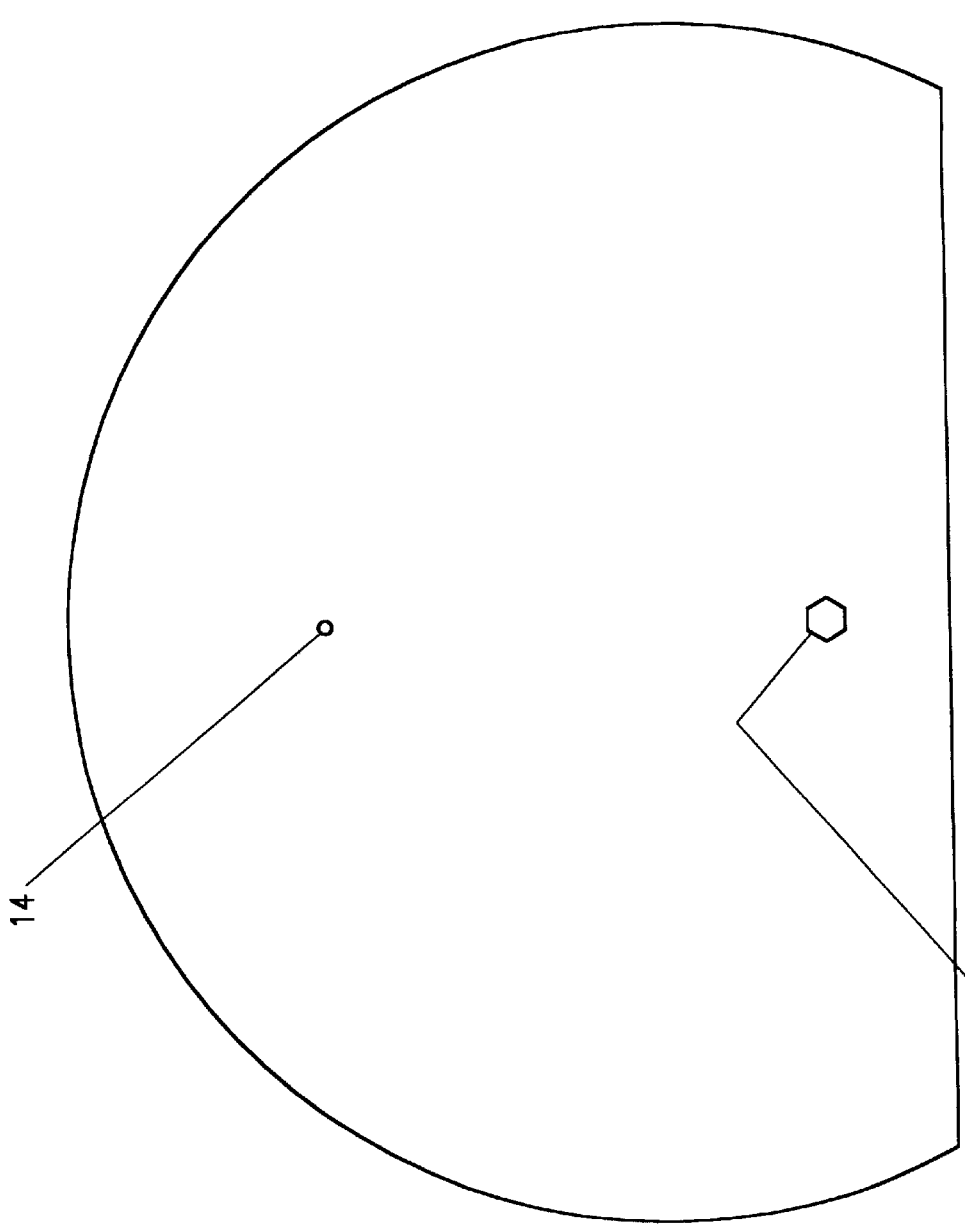
FIG. 4 is the rear view if the back plate in FIG. 1.
FIG. 5 is the side view of the back plate in FIG. 1.
Figure 6:
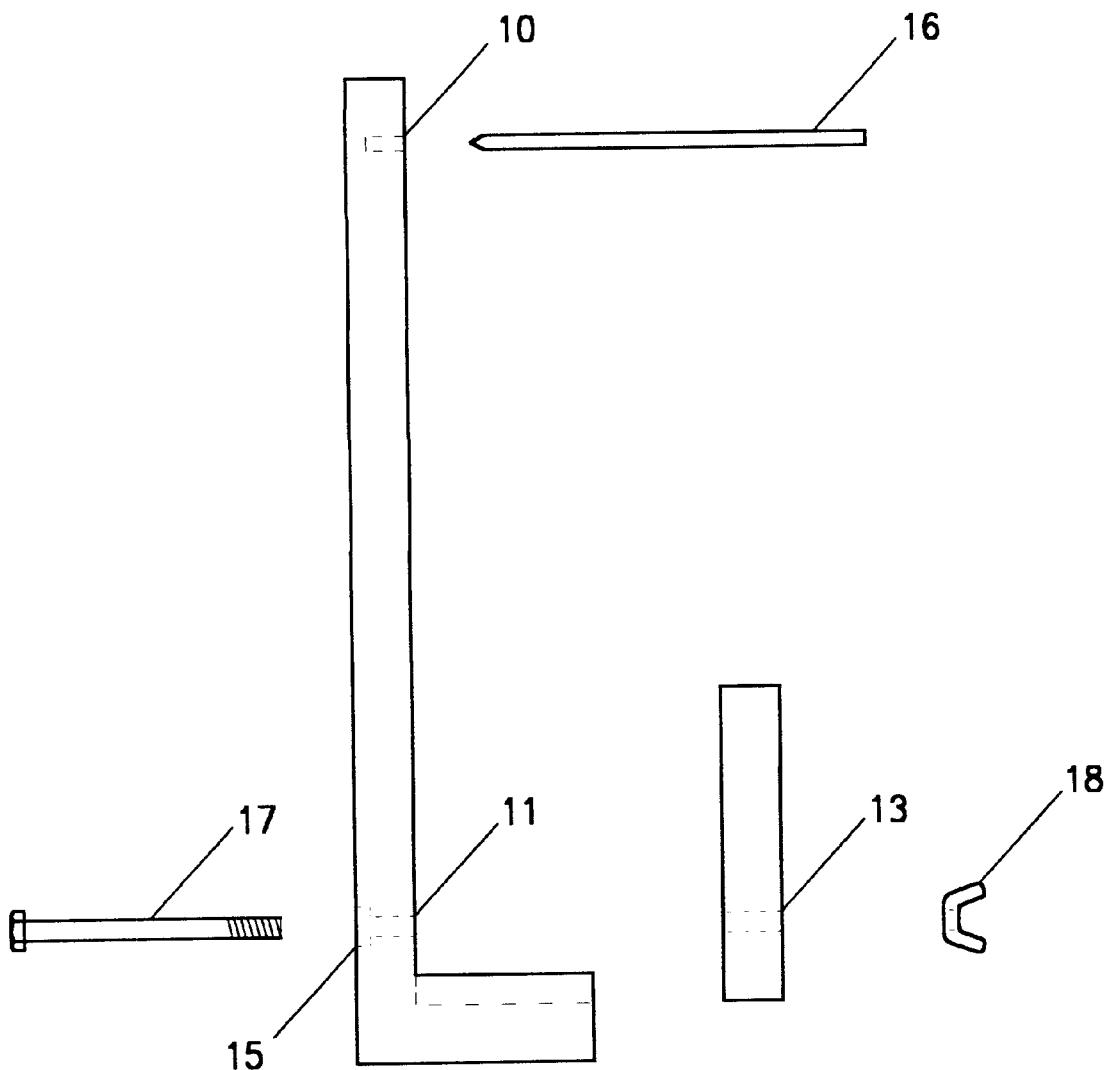
FIG. 6 is the side view of a bolt, a back plate in FIG. 1, a dowel, a stabilizing block in FIG. 2, and a wing nut, in the order of assembly and use.

The present invention includes a flat surface (back plate) with a chemical tray 12, as depicted in FIG. 1. The present invention also includes a stabilizing block as depicted in FIG. 2. Included in FIG. 6, is a dowel 16, a bolt 17, and a wing nut 18. Referring to FIG. 1, the front of the back plate has a single hole 11 preferably ¼" in diameter, and a plurality of holes 10 preferably 1/16" in diameter. The single hole 11 penetrates completely through the back plate, while the pluralities of holes 10 are in a matrix pattern, at a preferred depth of ¾ the thickness of the back plate. The plurality of dowels 16 in FIG. 6 is of a diameter such that, when inserted into the plurality of holes 10 on the front of the back plate in FIG. 1 fit securely. In FIG. 6, the bolt 17 is of the same diameter, or smaller, as the larger hole 11 in the back plate and the hole 13 in the stabilizing block. The indention in the hole 15 is the shape and size of the bolt 17 head. This enables the bolt 17 to fit flush with the surface of the backside of the back plate, and also keeps the bolt 17 secure while the wing nut 18 is fastened. The bolt is placed through the hole 15 in FIG. 4 of the back plate, and then the hole 13 in the stabilizing block in FIG. 2, starting from the rear of the back plate in FIG. 4. The wing nut 18 in FIG. 6 is screwed on the bolt 17, securing the stabilizing block to the back plate.

Figure 3:
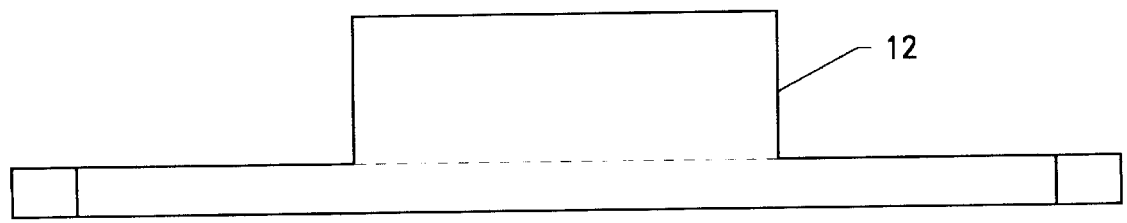
FIG. 3 is the bottom view of the back plate in FIG. 1.

Referring to FIG. 6, the bolt 17 head is placed in the hole 15 such that the bolt 17 head is flush with the rear of the back plate. The back plate is laid flat on it's back as depicted in FIG. 3. Referring back to FIG. 6, the turkey tail is laid on the front of the back plate with the meaty part against the bolt 17 that is protruding from the hole 11 in the back plate. The primary turkey tail feathers are placed in a desired position individually by inserting the dowels 16 into a corresponding partially penetrating hole 10 on the front of the back plate, thus tacking the feather in place. This step is repeated one primary tail feather at a time, until the turkey tail has the desired drying formation. It is preferable to start with the outermost primary tail feathers first. The chemical is then placed on the meaty portion of the turkey tail. The hole 13 in the stabilizing block is placed on the bolt 17 that is protruding from the back plate. This enables the stabilizing block to slide into the chemical tray 12. The wing nut 18 is place on the bolt 17 and tightened until there is sufficient pressure to secure the turkey tail and stabilizing block to the back plate. The turkey tail and device can then be placed in the upright position and stored in a small space, or hung from a nail or screw inserted into the hanger slot 14 in FIG. 4, for the drying duration.

In compliance with the statute, the invention has been described in language more or less specific as to the structural and methodical features. It is to be understood, however, that the invention is not limited to the specific features shown and described, since the means herein disclosed comprise preferred forms of putting the invention into effect. The invention is, therefore, claimed in any of its forms or modifications with the proper scope of the appended claims appropriately interpreted in accordance with the doctrine of equivalents.

I claim:

1. An apparatus used in a drying or curing process of a turkey tail with a meat portion and at least one of a plurality of feathers comprising:

a mounting plate with a flat surface for mounting the turkey tail, wherein the mounting plate has a front face, a back face, an upper quadrant and a lower quadrant;

a plurality of holes arranged in a matrix pattern on the front face of the mounting plate, wherein the plurality of holes partially penetrates the mounting plate;

at least one dowel for inserting in at least one of a plurality of holes of the mounting plate to tack at least one of a plurality of feathers during the drying or curing process, wherein the at least one dowel is of a diameter to fit snugly and securely into at least one of a plurality of holes in the mounting plate;

a chemical tray on the front face of the mounting plate, wherein the chemical tray contains an overflow of powder or liquid chemicals used in the drying or curing process;

a stabilizing block mounted on the front face of the mounting plate for keeping the turkey tail securely mounted to the mounting plate during the drying or curing process, wherein the stabilizing block slides into the chemical tray;

a first hole located in the lower quadrant of the mounting plate, wherein the first hole completely penetrates the mounting plate;

a second hole located in the stabilizing block, wherein the second hole completely penetrates the stabilizing block and the second hole has a location corresponding to a location of the first hole;

a bolt that penetrates the first hole and the second hole;

a wing nut for screwing onto the bolt to secure the stabilizing block to the mounting plate; and a hanger slot on the back face of the mounting plate.

2. The apparatus of claim 1 wherein at least one of the first hole and the second hole preferably has a diameter of 0.25 inches.

3. The apparatus of claim 2 wherein the bolt preferably has a diameter of less than or equal to 0.25 inches.

4. The apparatus of claim 1 wherein the plurality of holes on the front face of the mounting plate preferably has a depth of 75% of the thickness of the mounting plate.

5. The apparatus of claim 1 wherein the plurality of holes on the front face of the mounting plate preferably has a diameter of 0.0625 inches.

6. The apparatus of claim 5 wherein the at least one dowel preferably has a diameter of less than or equal to 0.0625 inches.

7. The apparatus of claim 1 wherein the bolt fits flush with the back face of the mounting plate.

8. The apparatus of claim 1 wherein the bolt is first inserted through the first hole and then inserted through the second hole.

9. The apparatus of claim 1 wherein the mounting plate is laid flat on the back face before the turkey tail is mounted on the mounting plate.

10. The apparatus of claim 1 wherein at least one of the plurality of feathers is placed in a position individually by inserting at least one dowel into at least one of a plurality of holes on the front surface of the mounting plate corresponding to the position of the at least one plurality of feathers.

11. The apparatus of claim 1 wherein the turkey tail is mounted on the front face of the mounting plate with the meat portion against the bolt.

12. The apparatus of claim 11 wherein the powder or liquid chemicals used in the drying or curing process are placed on the meat portion.

13. The apparatus of claim 12 wherein the apparatus is placed in an upright position after the powder or liquid chemicals are placed on the meat portion.

14. The apparatus of claim 12 wherein the apparatus is hung from the hanger slot after the powder or liquid chemicals are placed on the meat portion.

15. The apparatus of claim 12 wherein the powder or liquid chemicals are salt or bleach.

* * * * *